United States Patent [19]

Matsuura et al.

[11] Patent Number: 4,945,186

[45] Date of Patent: Jul. 31, 1990

[54] METHOD OF PRODUCING 3-BROMOBENZALDEHYDE

[75] Inventors: Shinichi Matsuura; Osamu Miyano, both of Shin-nanyo, Japan

[73] Assignee: Toso Organic Chemical Co., Ltd., Tokyo, Japan

[21] Appl. No.: 455,782

[22] Filed: Jan. 2, 1990

Related U.S. Application Data

[63] Continuation of Ser. No. 172,803, Mar. 28, 1988, abandoned.

[30] Foreign Application Priority Data

Aug. 25, 1987 [JP] Japan ................... 62-211198

[51] Int. Cl.$^5$ .............................................. C07C 45/00
[52] U.S. Cl. ..................................... 568/433; 570/254
[58] Field of Search ......................... 568/433; 570/254

[56] References Cited

U.S. PATENT DOCUMENTS

| | | | |
|---|---|---|---|
| 3,961,033 | 6/1976 | Kleiman et al. | 570/254 |
| 4,036,887 | 7/1977 | Sheldon et al. | 568/433 |
| 4,551,557 | 11/1985 | Ratton et al. | 568/433 |
| 4,551,558 | 11/1985 | Ratton et al. | 568/433 |
| 4,585,898 | 4/1986 | Lau et al. | 568/433 |

FOREIGN PATENT DOCUMENTS 52-77021 6/1977 Japan .................... 568/433

OTHER PUBLICATIONS

Organic Preparations and Procedures Int. 6(5), 251–253 (1974), "An Improved Procedure for the Meta-Bromination of Aromatic Carbonly Compounds".
Journal of Organic Chemistry, vol. 23, 1412 (1958), "The Swamping Catalyst Effect. II. Nuclear Halogenation of Aromatic Aldehydes and Ketones".

*Primary Examiner*—Bruce Gray
*Attorney, Agent, or Firm*—Oblon, Spivak, McClelland, Maier & Neustadt

[57] ABSTRACT

A method of producing 3-bromobenzaldehyde is disclosed, wherein, upon producing 3-bromobenzaldehyde by allowing benzaldehyde to react with bromine in the presence of brominating catalyst in 1,2-dichloroethane being a reaction solvent, 1,2-dichloroethane having been used for aforesaid reaction as a reaction solvent is recovered and, after the recovered solvent is allowed first to react with chlorine in the presence of above brominating catalyst, the reaction is performed by the addition of benzaldehyde and bromine. Foregoing 1,2-dichloroethane recovered may be brought to the reaction with chlorine with or without adding fresh 1,2-dichloroethane and above brominating catalyst is preferably aluminum chloride.

10 Claims, No Drawings

METHOD OF PRODUCING 3-BROMOBENZALDEHYDE

This application is a Continuation of application Ser. No. 172,803 filed on Mar. 28, 1988, now abandoned.

BACKGROUND OF THE INVENTION

The present invention relates to a novel method of producing 3-bromobenzaldehyde. 3-Bromobenzaldehyde obtainable from the present invention is an useful substance as a raw material for the insecticides of synthesized pyrethroid type.

As a conventional method, there is one described in Japanese Unexamined Patent Publication No. Sho 51-143639. According to this disclosure, benzaldehyde is allowed to react with bromine at a temperature below about 100° C. in the presence of chlorinated hydrocarbon solvent and brominating catalyst and the amount of brominating catalyst used is at least 1 mole per mole of the benzaldehyde.

In this method, 3-chlorobenzaldehyde, which is a by-product, is formed partially because of the use of chlorine and yet the starting material is left behind in amounts not less than 10%. Thus, this method is hard to say to be efficient.

For this reason, the theme of the invention lies in finding a method to produce 3-bromobenzaldehyde by improvement of the shortcomings of the methods known in public, which are partial formation of 3-chlorobenzaldehyde being a by-product and remaining considerable amounts of unreacted benzaldehyde.

As a result of diligent studies aiming at the development of an excellent method for the synthesis of 3-bromobenzaldehyde, the inventors have found that, upon reacting bromine with benzaldehyde in 1,2-dichloroethane being a reaction solvent in the presence of brominating catalyst, 1,2-dichloroethane changes partially into 1-bromo-2-chloroethane and 1,2-dibromoethane and bromine used is not released out of the system at all. Thus, this solvent recovered was allowed to react with chlorine in the presence of brominating catalyst, it was surprisingly found that 1-bromo-2-chloroethane and 1,2-dibromoethane were regenerated to 1,2-dichloroethane and yet bromine was generated. Based on this discovery, a method of producing 3-bromobenzaldehyde has been completed, leading to the present invention.

SUMMARY OF THE INVENTION

The main point of the invention is a method of producing 3-bromobenzaldehyde characterized in that, upon producing 3-bromobenzaldehyde by allowing benzaldehyde to react with bromine in the presence of brominating catalyst in 1,2-dichloroethane being a reaction solvent, 1,2-dichloroethane having been used for above reaction as a reaction solvent is recovered and, after the solvent is allowed first to react with chlorine in the presence of above brominating catalyst, the reaction is performed by the addition of benzaldehyde and bromine subsequently.

DETAILED DESCRIPTION OF THE INVENTION

According to the invention, after the reaction have finished, 1,2-dichloroethane being a reaction solvent changes into 1-bromo-2-chloroethane and 1,2-dibromoethane, playing apparently a role as a bromine carrier, and expensive bromine does not come out of the system at all. In addition, the recovered solvent can be regenerated again to 1,2-dichloroethane by allowing to react with chlorine in the presence of brominating catalyst, thereby generating bromine. Therefore, in the second and subsequent reaction, an amount of bromine having been consumed for 3-bromobenzaldehyde has only to be compensated at all times. As a result, since 3-chlorobenzaldehyde is not formed and yet the conversion rate of benzaldehyde is also not less than 99%, it is possible to obtain 3-bromobenzaldehyde at higher selectivity and also with higher yield and higher quality compared with conventional methods. Thus, the method of the invention can be said to be excellent economically.

In the invention, as the brominating catalysts, Lewis acids such as aluminum chloride, ferric chloride, etc. can be mentioned, but aluminum chloride is preferable due to higher reactivity. Moreover, the molar ratio of brominating catalyst to benzaldehyde is 1:1 to 1.5:1, preferably 1.2:1 to 1.4:1. The molar ratio of bromine to benzaldehyde is 1:1 to 1.1:1 and the use of bromine being a little excessive from the theoretical amount is preferable.

Furthermore, the starting concentration of benzaldehyde in 1,2-dichloroethane is preferably to be 1 to 5 mol/liter, in particular, 2 to 3 mol/liter. The temperature of bromination is 0° to 60° C., preferably 30° to 50° C.

When the reaction solvent is recovered and used for the second reaction, all solvents are regenerated to 1,2-dichloroethane by chlorine. Chlorine used at this time may be introduced in a gaseous form or added dropwise by dissolving into suitable solvents. The temperature at that time is 0° to 50° C., preferably 20° to 30° C.

The invention will be illustrated in more detail based on the following examples, but it is not confined to only these examples.

EXAMPLE 1

To a mixture of 1,2-dichloroethane (250 g) with 98% aluminum chloride (0.65 mol, 88.6 g) was added 97% benzaldehyde (0.50 mol, 54.6 g) over 1 hour at 40° C. After bromine (0.55 mol, 88.0 g) was added over 2 hours at 40° C., this mixture was stirred for 2 hours at the same temperature. After the reaction mixture being added to ice water (375.0 g) and stirred thoroughly, this was allowed to stand and separated. The organic phase was washed with 100 ml of water, further with 100 ml of 0.5% aqueous solution of sodium carbonate, and finally with 100 ml of water. Then, 241.0 g of solvent were recovered and the residue was distilled, obtaining 83.5 g of 3-bromobenzaldehyde.

EXAMPLE 2

Into a mixture of 1,2-dichloroethane (1,2-dichloroethane: 173.7 g, 1-bromo-2-chloroethane: 63.5 g, 1,2-dibromoethane: 2.2 g) and recovered from Example 1 with 98% aluminum chloride (0.365 mol, 88.6 g) was blown chlorine (0.25 mol, 17.8 g) at 25° C., and 97% benzaldehyde (0.50 mol, 54.6 g) was added over 1 hour at 40° C. After bromine (0.30 mol, 48.0 g) was added dropwise to this mixture over 2 hours at 40° C., the resulting mixture were stirred for 2 hours at that temperature. The post-treatment was carried out by the similar procedure to that in Example 1. As a result, 82.8 g of 3-bromobenzaldehyde were obtained.

EXAMPLE 3

To 1,2-dichloroethane (1,2-dichloroethane: 143.8 g, 1-bromo-2-chloroethane: 60.5 g, 1,2-dibromoethane: 4.8 g) recovered from Example 2 was added fresh 1,2-dichloroethane (41.5 g), and 98% aluminum chloride (0.65 mol, 88.6 g) was mixed. Into this was blown chlorine (0.25 mol, 17.8 g) at °C., and 97% benzaldehyde (0.50 mol, 54.6 g) was added over 1 hour at 40° C. After bromine (0.30 mol, 48.0 g) was added dropwise to this mixture over 2 hours at 40° C., the resulting mixtures were stirred for 2 hours at that temperature. The post-treatment was carried out by the similar procedure to that in Example 1. As a result, 83.1 g of 3-bromobenzaldehyde were obtained.

The method of the present invention has many excellent advantages. Since 1,2-dichloroethane, that is, acts apparently as a bromine carrier, and expensive bromine does not come out the system at all, and it becomes possible to generate bromine again from the recovered solvent, bromine can be utilized at maximum.

From the reasons above, the by-product is not formed and the conversion rate of benzaldehyde also becomes very high. Therefore, the method of the invention can be said to have higher selectivity and higher yield and to be far more excellent compared with conventional methods.

What is claimed is:

1. A method of producing 3-bromobenzaldehyde, comprising:
    initially brominating benzaldehyde with molecular bromine in 1,2-dichloroethane solvent in the presence of a bromonating catalyst thereby producing the desired 3-bromobenzaldehyde product and unavoidably converting significant quantities of 1,2-dichloroethane solvent to 1,2-bromochloroethane and 1,2-dibromoethane;
    recovering said 3-bromobenzaldehyde product and isolating the converted solvent containing brominating catalyst;
    treating the converted solvent with molecular chlorine in the presence of brominating catalyst, thereby representing 1,2-dichloroethane solvent and molecular bromine; and
    continuing the desired brominating reaction, which produces 3-bromobenzaldehyde, by the addition of molecular bromine and benzaldehyde to the regenerated solvent and molecular bromine.

2. The method of claim 1, wherein said brominating catalyst is a Lewis acid catalyst.

3. The method of claim 2, wherein said Lewis acid catalyst is aluminum chloride or ferric chloride.

4. The method of claim 3, wherein said catalyst is aluminum chloride.

5. The method of claim 1, wherein the molar ratio of brominating catalyst to benzaldehyde reactant ranges from 1:1 to 1.5:1.

6. The method of claim 5, wherein said ratio ranges from 1.2:1 to 1.4:1.

7. The method of claim 1, wherein the molar ratio of bromine to benzaldehyde ranges from 1:1 to 1.1:1.

8. The method of claim 1, wherein the temperature during bromination ranges from 0° to 60° C.

9. The method of claim 8, wherein said temperature ranges from 30° to 50° C.

10. The method of claim 1, wherein during the regeneration of said solvent by the addition of chlorine, the temperature of the regeneration process ranges from 0° to 50° C.

* * * * *